United States Patent
Lee et al.

(10) Patent No.: US 10,980,735 B2
(45) Date of Patent: Apr. 20, 2021

(54) EXTERNALLY-APPLIED DERMAL PREPARATION COMPOSITION CONTAINING EXTRACT OF GREEN TEA CULTIVATED UNDER EXTREME SHADING

(71) Applicant: AMOREPACIFIC CORPORATION, Seoul (KR)

(72) Inventors: Yeong Ran Lee, Yongin-si (KR); Jun Seong Park, Yongin-si (KR); Eun Soo Lee, Yongin-si (KR); Nok Hyun Park, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 16/338,226

(22) PCT Filed: Sep. 21, 2017

(86) PCT No.: PCT/KR2017/010378
§ 371 (c)(1),
(2) Date: Mar. 29, 2019

(87) PCT Pub. No.: WO2018/062762
PCT Pub. Date: Apr. 5, 2018

(65) Prior Publication Data
US 2020/0030225 A1     Jan. 30, 2020

(30) Foreign Application Priority Data
Sep. 30, 2016 (KR) .................... 10-2016-0126827

(51) Int. Cl.
| | |
|---|---|
| *A61K 36/82* | (2006.01) |
| *A61K 8/9789* | (2017.01) |
| *A61Q 17/00* | (2006.01) |
| *A61Q 19/00* | (2006.01) |
| *A61Q 19/08* | (2006.01) |
| *A61Q 19/10* | (2006.01) |

(52) U.S. Cl.
CPC ............ *A61K 8/9789* (2017.08); *A61K 36/82* (2013.01); *A61Q 17/00* (2013.01); *A61Q 19/00* (2013.01); *A61Q 19/007* (2013.01); *A61Q 19/08* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 7,611,741 B2 | 11/2009 | Honda et al. | |
| 2005/0008753 A1 | 1/2005 | Honda et al. | |
| 2009/0012155 A1 | 1/2009 | Kim et al. | |
| 2010/0317736 A1* | 12/2010 | Shin ................. | A61Q 19/08 514/563 |
| 2011/0124595 A1* | 5/2011 | Kwon ............... | A61K 8/73 514/54 |
| 2016/0175217 A1 | 6/2016 | Kim et al. | |

FOREIGN PATENT DOCUMENTS

| | | |
|---|---|---|
| KR | 2003 087105 A | * 11/2003 |
| KR | 10-2007-0028901 | 3/2007 |
| KR | 10-2009-0064743 | 6/2009 |
| KR | 10-2010-0059995 | 6/2010 |
| KR | 10-2013-0130337 | 12/2013 |

OTHER PUBLICATIONS

Yang, Z. et al. Charcterisation of Volatile and Non-Volatile Metabolites in Etiolated Leaves of Tea Plants in the Dark. Food Chemistry 135(4)2268-2276, Dec. 2012. (Year: 2012).*
Li Y. et al. Metabolic Regulation Profiling of Carbon and Nitrogen in Tea Plants in Response to Shading. J of Agricultural and Food Chemistry 68(4)962-974, Jan. 29, 2020. (Year: 2020).*
International Search Report for PCT/KR2017/010378 dated Jan. 15, 2018 (PCT/ISA/210).
Korea Food Research Institute, "Production of High Quality Matcha for Substitution of Japanese Matcha and Developing a New Product", Ministry of Agriculture, Food and Rural Affairs, R&D report, Dec. 2011, pp. 1-173 with partial English translation.
Lee et al., "Study on Shade Culture for Quality and Quantity of Leaf in Tea Plant(*Camellia sinensis* L.)", The Korea Tea Society, vol. 15, No. 1, Apr. 2009, pp. 99-105 with partial English translation.

* cited by examiner

*Primary Examiner* — Ralph J Gitomer
(74) *Attorney, Agent, or Firm* — Sughrue Mion, PLLC (57) ABSTRACT

The present invention relates to a skin external composition containing an extract of green tea produced by an extreme light-shielding cultivation method, which is distinguished from a conventional light-shielding cultivation method of green tea. More specifically, the present invention relates to a skin external composition, which contains an extract of green tea cultivated by extreme light-shielding, in which the amino acid content is remarkably increased by cultivating the green tea by a light-shielding cultivation under a light-shielding rate of 99% or more, thereby obtaining more excellent skin moisturizing, skin protecting, and anti-aging effects.

10 Claims, 3 Drawing Sheets
(1 of 3 Drawing Sheet(s) Filed in Color)

EXTERNALLY-APPLIED DERMAL PREPARATION COMPOSITION CONTAINING EXTRACT OF GREEN TEA CULTIVATED UNDER EXTREME SHADING

CROSS REFERENCE TO RELATED APPLICATIONS

This application is a National Stage of International Application No. PCT/KR2017/010378 filed Sep. 21, 2017, claiming priority based on Korean patent Application No. 10-2016-126827, filed Sep. 30, 2016.

TECHNICAL FIELD

The present invention relates to a skin external composition containing an extract of green tea produced by an extreme light-shielding cultivation method, which is distinguished from a conventional light-shielding cultivation method of green tea. More specifically, the present invention relates to a skin external composition, which contains an extract of green tea cultivated by extreme light-shielding, in which the amino acid content is remarkably increased by cultivating the green tea by a light-shielding cultivation under a light-shielding rate of 99% or more, thereby obtaining more excellent skin moisturizing, skin protecting, and anti-aging effects.

BACKGROUND ART

Light-shielding cultivation is a method of cultivating a tea by blocking light (light-shielding rate of 50 to 70%) for a certain period of time during growth of tea buds. When teas are cultivated under light-shielding, the hardening of tea leaves can be delayed, the green pigment can be intensified, the catechin content can be reduced, and the contents of amino acid and the anine can be increased. Thus, in order to make green tea that is soft by reducing the astringent taste of the green tea, and darker in color, that is, to improve aesthetic, taste, etc., the light-shielding cultivation method has been selected as a method for improving the availability of green tea as a food.

In contrast, an extreme light-shielding cultivation method is a method for cultivating a tea under a light-shielding rate of 90% or more, preferably 95% or more, particularly 99% or more based on the light-shielding cultivation method. When green tea is cultivated by the extreme light-shielding cultivation method, the yield of green tea is remarkably decreased, which is not desirable in view of productivity and cost. Rather, chlorosis occurs in the leaves of green tea, and thereby causes deterioration of visual quality, and also, the content of catechin tends to decrease. Therefore, the availability of green tea cultivated by the extreme light-shielding cultivation method is remarkably decreased as existing food at the application level.

Meanwhile, skin external compositions containing conventional green tea have been developed based on the antioxidant and anti-inflammatory effects derived from catechin, which accounts for large amounts of the components in green tea. However, in addition to catechin, green tea contains various kinds of amino acids that can exhibit various skin effects, and the contents thereof can be increased by the light-shielding cultivation as described above.

However, the conventional light-shielding cultivation method having a light-shielding rate of 50 to 70% has a limitation in increasing the contents of amino acids, and green tea cultivated by the light-shielding cultivation method is only available as food in most cases. Further, research and development on use of green tea as a skin external application are insufficient.

Meanwhile, a conventional extraction method utilizes a small amount of organic solvents so that it is difficult to maximize the amino acid contents. Thus, there is a need for an extraction method that can maximize the extraction of amino acids.

DETAILED DESCRIPTION OF THE INVENTION

Technical Problem

The present inventors have found that when green tea is cultivated by an extreme light-shielding cultivation method, the amino acid content is remarkably increased, and that, when an extract of green tea cultivated by extreme light-shielding is used as an active ingredient for a skin external composition, it can provide more excellent skin moisturizing, skin protecting, and anti-aging effects compared to a skin external composition containing an extract of green tea cultivated by conventional no light-shielding or light-shielding, thereby completing the present invention.

Accordingly, it is one object of the present invention to provide a skin external composition for skin moisturization, anti-aging or skin barrier protection containing an extract of green tea cultivated by an extreme light-shielding cultivation method.

Technical Solution

In order to achieve the object above, one aspect of the present invention provides a skin external composition for skin moisturization, anti-aging or skin barrier protection containing an extract of green tea cultivated under a light-shielding rate of 90% or more.

Further, another aspect of the present invention provides use of an extract of green tea cultivated by an extreme light-shielding cultivation method under a light-shielding rate of 90% or more as a skin moisturizing agent, a skin anti-aging agent, a skin wrinkle-improving agent, a skin elasticity-improving agent, a skin barrier function-enhancing agent, or skin damage-suppressing or skin protecting agent, in the preparation of a skin external composition.

Advantageous Effects

The method of the present invention can provide more excellent effects in increasing skin moisturizing powder, anti-aging or skin barrier protection by containing an extract of green tea in which the amino acid content is remarkably increased by cultivating the green tea by an extreme light-shielding cultivation method under a light-shielding rate of 90% or more, compared to a composition containing a conventional green tea extract.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

The present invention relates to a skin external composition containing an extract of green tea cultivated by an extreme light-shielding cultivation method as an active ingredient.

As used herein, the term "extreme light-shielding cultivation method" refers to a method for cultivating a plant under a light-shielding rate of 90% or more, preferably 95% or more, more preferably 98% or more, even more preferably 99% or more, and still even more preferably 99.9% or more based on the light-shielding cultivation method.

The extreme light-shielding cultivation of the green tea (Camellia sinensis L.) of the present invention is a method for cultivating Camellia sinensis L. for a duration of 10 days or more, preferably 10 to 25 days, more preferably 15 to 21 days under a light-shielding rate of 90% or more, preferably 95% or more, more preferably 98% or more, even more preferably 99% or more, and still even more preferably 99.9% or more. Further, the extreme light-shielding cultivation method of the present invention is carried out by light-shielding of Camellia sinensis L. at 1 stem-1 leaf stage to 1 stem-4 leaf stage, more preferably at 1 stem-1 leaf stage to 1 stem-3 leaf stage, more preferably at 1 stem-1 leaf stage, but is not limited thereto.

By using the extreme light-shielding cultivation method of the present invention, the total amino acid content present in the green tea can be remarkably increased.

The extract of the green tea cultivated by extreme light-shielding used in the present invention is obtained by extracting green tea leaves or powder of green tea leaves cultivated by the extreme light-shielding cultivation method using water or a lower alcohol, preferably water or ethanol, as an extraction solvent.

The extract may be used as it is in an extracted form obtained from the green tea leaves, or may be used in a powder form prepared by drying and pulverizing the material obtained from the extraction.

Further, in consideration of its application to a cosmetic composition, water is preferably used as an extraction solvent. In particular, when water is used as an extraction solvent, the elution rate of amino acid increases as compared to a case where other extraction solvent is used. Further, in case of leaching or a hot water extraction, the extraction level of components other than amino acids becomes higher, and therefore, a low-temperature low-speed water extraction (for example, using a Dutch coffee maker) is more desirable in terms of selective elution of amino acids.

In the present invention, the content of the extract of green tea cultivated by extreme light-shielding is not limited, but is preferably 0.0001 to 40% by weight, preferably 0.01 to 30% by weight, more preferably 0.1 to 20% by weight based on the total amount of the composition. When the content is less than 0.0001% by weight, it may be difficult to function as an active ingredient, and when the content is more than 40% by weight, the formulation stability may be deteriorated, and thus is not desirable.

The composition according to the present invention maintains skin moisture and increases water retention capacity by promoting the differentiation of keratinocytes or promoting the expression of transglutaminase, thereby providing a skin moisturizing effect.

The composition according to the present invention improves skin wrinkles and increases skin elasticity by suppressing skin damage caused by oxidation or ultraviolet rays, promoting collagen production or inhibiting biosynthesis of matrix metalloproteinase 1 (MMP-1), thereby providing an anti-aging effect.

The composition according to the present invention provides a skin protecting effect by suppressing skin damage. Herein, the skin includes scalp or hair. That is, the composition of the present invention also provides an effect of protecting the hair by suppressing the damage of the scalp or hair.

The composition according to the present invention provides a skin protecting effect by suppressing skin damage caused by oxidation or ultraviolet rays. Herein, the skin includes scalp or hair. That is, the composition of the present invention also provides an effect of protecting the scalp or hair by suppressing the damage of the scalp or hair caused by oxidation or ultraviolet rays.

Further, the present invention provides use of an extract of green tea cultivated by an extreme light-shielding cultivation method under a light-shielding rate of 90% or more as a skin moisturizing agent, a skin anti-aging agent, a skin wrinkle-improving agent, a skin elasticity-improving agent, a skin barrier function-enhancing agent, or a skin damage-suppressing or skin protecting agent, in the preparation of a skin external composition.

The skin external composition according to the present invention may be formulated into a cosmetic composition or a pharmaceutical composition.

The cosmetic composition according to the present invention may contain a cosmetically or dermatologically acceptable medium or base. It may be provided in any form suitable for topical application, for example, in the form of solutions, gels, solids, paste anhydrous products, emulsions obtained by dispersing oil phase in aqueous phase, suspensions, microemulsions, microcapsules, microgranules or ionic (liposomes) and non-ionic vesicle dispersants, or in the form of creams, skins, lotions, powders, ointments, sprays or conceal sticks. These compositions may be prepared according to a conventional method in the art. The composition according to the present invention may also be used in the form of a foam or an aerosol composition further containing a compressed propellant.

The cosmetic composition according to the present invention may contain adjuvants commonly used in the field of cosmetic or dermatological science such as fatty substances, organic solvents, solubilizing agents, thickening agents, gelling agents, softening agents, antioxidants, suspending agents, stabilizing agents, foaming agents, flavoring agents, surfactants, water, ionic or non-ionic emulsifiers, fillers, sequestering agents, chelating agents, preservatives, vitamins, blockers, wetting agents, essential oils, dyes, pigments, hydrophilic or lipophilic active agents, lipid vesicles or any other ingredient commonly used in cosmetics. Such adjuvants are introduced in the amounts commonly used in the fields of cosmetic or dermatological science.

The skin external composition according to the present invention is not particularly limited by its formulation, and for example, it may be formulated into cosmetics such as softening cosmetic water, astringent cosmetic water, nourishing cosmetic water, nourishing cream, massage cream, essence, eye cream, eye essence, cleansing cream, cleansing foam, cleansing water, facial pack, powder, body lotion, body cream, body oil and body essence, etc.

The skin external composition according to the present invention may be a pharmaceutical composition. The pharmaceutical composition may further contain a pharmaceutical adjuvant such as preservatives, stabilizers, hydrating agents, emulsifying accelerators, salts for controlling osmotic pressure and/or buffers etc., and other therapeutically useful substances. The pharmaceutical composition may be formulated into lotions, creams, ointments or gels.

The pharmaceutical composition may be preferably administered via a transdermal route.

The dose of the extract of green tea cultivated by extreme light-shielding, which is an active ingredient of the pharmaceutical composition, will vary depending on the age, sex and body weight of a subject to be treated, a particular disease or pathological condition to be treated, the severity of the disease or pathological condition, the administration route and the discretion of a prescriber.

Determination of the dose based on these factors is in the level of those skilled in the art. A general dose may be in the range of 0.0001 mg/kg/day to about 2000 g/kg/day.

MODE FOR CARRYING OUT THE INVENTION

Hereinafter, the constitutions and effects of the present invention will be described in detail by way of Examples and Test Examples shown below. However, these Examples and Test Examples are given for illustrative purposes only to help understanding of the present invention, and the scope of the invention is not intended to be limited to or by these Examples and Test Examples.

[Example 1] Preparation of Extract of Green Tea Cultivated by Extreme Light-Shielding (Light-Shielding Rate of 99%) Using 70% Ethanol Green tea (*Camellia sinensis* L.) cultivated by an extreme light-shielding treatment with a light-shielding rate of 99% (light-shielding duration of 1 day (which is the starting day, the rest is the same as above), 5 days, 10 days, 15 days, 20 days and 25 days) was washed with purified water, dried and then finely powdered to obtain green tea powder cultivated by extreme light-shielding. 100 g of the green tea powder thus obtained was added to 1 liter of a 70% aqueous ethanol solution, extracted for 12 hours while stirring, and then filtered through a Whatman filter paper No. 2. The extract thus obtained was concentrated under reduced pressure at 50° C. using a distillation apparatus equipped with a cooling condenser and dried to obtain an extract of green tea (dry weight of 30.85 g) cultivated by extreme light-shielding (light-shielding rate of 99%) using 70% ethanol.

[Example 2] Preparation of Extract of Green Tea Cultivated by Extreme Light-Shielding (Light-Shielding Rate of 99%) Through Low-Speed and Low-Temperature Extraction Using Water Green tea cultivated by an extreme light-shielding treatment with a light-shielding rate of 99% (light-shielding duration of 1 day, 5 days, 10 days, 15 days, 20 days and 25 days) was washed with purified water, dried and then finely powdered to obtain green tea powder cultivated by extreme light-shielding. In a cylindrical glass bottle equipped a discharge port at the lower part, a Whatman filter paper No. 2 was laid, and 100 g of green tea powder cultivated by extreme light-shielding was placed thereon. Then, a paper filter was laid on top of the powder, and the droplets of water was allowed to drip to evenly wet the surface. A water bottle equipped with a speed-adjustable valve was placed on top of the cylindrical glass bottle, and a mixture of purified water and ice made with purified water was added thereto to maintain the temperature at 4° C. or less. The process of dripping water droplets from the water bottle to the cylindrical glass bottle was continued for 10 hours at a rate of about 100 mL per hour (a total of 1000 mL of water was used for extraction). The extracts of green tea obtained by extreme light-shielding discharged from the lower part of the cylindrical glass bottle were collected, concentrated under reduced pressure at 50° C. using a distillation apparatus equipped with a cooling condenser and freeze-dried to obtain an extract of green tea (dry weight of 26.21 g) cultivated by extreme light-shielding (light-shielding rate of 99%) through a low-speed and low-temperature extraction using water.

[Example 3] Preparation of Extract of Green Tea Cultivated by Extreme Light-Shielding (Light-Shielding Rate of 90%) Through Low-Speed and Low-Temperature Extraction Using Water An extract of green tea (dry weight of 27.61 g) cultivated by extreme light-shielding through a low-speed and low-temperature extraction using water was obtained in the same manner as in Example 2, except that the green tea cultivated by extreme light-shielding with a light shielding rate of 90% was used.

[Example 4] Preparation of Extract of Green Tea Cultivated by Extreme Light-Shielding (Light-Shielding Rate of 95%) Through Low-Speed and Low-Temperature Extraction Using Water An extract of green tea (dry weight of 25.43 g) cultivated by extreme light-shielding (light shielding rate of 95%) through a low-speed and low-temperature using water was obtained in the same manner as in Example 2, except that the green tea cultivated by extreme light-shielding with a light shielding rate of 95% was used.

[Example 5] Preparation of Extract of Green Tea Cultivated by Extreme Light-Shielding (Light-Shielding Rate of 99%) Through Low-Temperature Leaching Using Water Green tea cultivated by an extreme light-shielding treatment with a light-shielding rate of 100% (light-shielding duration of 1 day, 5 days, 10 days, 15 days, 20 days and 25 days) was washed with purified water, dried and then finely powdered to obtain green tea powder cultivated by extreme light-shielding. 100 g of the green tea powder thus obtained was poured into 1 L of cold water of 4° C. or less obtained by mixing purified water and ice made with purified water, extracted for 12 hours while stirring, and then filtered through a Whatman filter paper No. 2. The extract thus obtained was concentrated under reduced pressure at 50° C. using a distillation apparatus equipped with a cooling condenser and dried to obtain an extract of green tea (dry weight of 23.25 g) cultivated by extreme light-shielding (light-shielding rate of 99%) through low-temperature leaching using water.

[Comparative Example 1] Preparation of Extract of Green Tea Cultivated without Light-Shielding Treatment Using 70% Ethanol Common green tea cultivated without light-shielding treatment was washed with purified water, dried and then finely powdered to obtain green tea powder cultivated without light-shielding treatment. 100 g of the green tea powder thus obtained was added to 1 liter of a 70% aqueous ethanol solution, extracted for 12 hours while stirring, and then filtered through a Whatman filter paper No. 2. The extract thus obtained was concentrated under reduced pressure at 50° C. using a distillation apparatus equipped with a cooling condenser and dried to obtain an extract of green tea (dry weight of 33.47 g) without light-shielding treatment using 70% ethanol.

[Comparative Example 2] Preparation of Extract of Green Tea Cultivated without Light-Shielding Treatment Through Low-Speed and Low-Temperature Extraction Using Water An extract of green tea (dry weight of 24.66 g) without light-shielding treatment through a low-speed and low-temperature extraction using water was obtained in the same manner as in Example 2, except that common green tea cultivated without light-shielding treatment was used.

[Comparative Example 3] Preparation of Extract of Green Tea Cultivated by General Light-Shielding Using 70% Ethanol Green tea cultivated by a general light-shielding treatment (light-shielding rate of 70%) was washed with purified water, dried and then finely powdered to obtain green tea powder cultivated by general light-shielding. 100 g of the green powder thus obtained was added to 1 liter of a 70% aqueous ethanol solution, extracted for 12 hours while stirring, and then filtered through a Whatman filter paper No. 2. The extract thus obtained was concentrated under reduced pressure at 50° C. using a distillation apparatus equipped with a cooling condenser and dried to obtain an extract of green tea (dry weight of 31.06 g) cultivated by general light-shielding using 70% ethanol.

[Comparative Example 4] Preparation of Extract of Green Tea Cultivated by General Light-Shielding Through Low-Speed and Low-Temperature Extraction Using Water An extract of green tea (dry weight of 29.87 g) cultivated by general light-shielding through low-speed and low-temperature extraction using water was obtained in the same manner as in Example 2, except that green tea cultivated by general light-shielding (light-shielding rate of 70%) was used.

[Test Example 1] Analysis of Total Amino Acid and Catechin Contents in Extracts (Difference According to Light-Shielding Rate and Light-Shielding Duration)

The total amino acid and catechin contents of the green tea extracts prepared in Examples 2 to 4 and Comparative Examples 2 and 4 (see Table 1 below for treatment conditions according to the light-shielding rate) were analyzed.

TABLE 1

Treatment conditions according to light-shielding rate

| Test Groups | Average intensity (Lux) | Light-shielding rate (%) |
| --- | --- | --- |
| No light-shielding | 104,433 | 0 |
| General light-shielding cultivation | 30,560 | 70 |
| Extreme light-shielding cultivation (90%) | 1,089 | 90 |
| Extreme light-shielding cultivation (95%) | 538 | 95 |
| Extreme light-shielding cultivation (99%) | 128 | 99 |

1. Analysis of Total Amino Acid Content

The amino acid content was determined by quantifying each of 22 kinds of free amino acids via a simultaneous analysis, and the total amount was determined. The extracts were dissolved in purified water to make a solution having a concentration of 10,000 ppm, and 20 μL of the solution was taken and added with 70 μL of the AccQ-Tag buffer and 20 μL of the AccQ-Tag derivative reagent, and subsequently, the mixture was mixed to prepare a test solution (AccQ-Tag buffer, derivative reagent, and solvent for UPLC analysis were purchased from Waters Corporation). For the mixtures of 22 amino acids, a derivatization reaction was carried out as the test solution by appropriately adjusting the concentration according to the content of each amino acid in the extract. The components of the test solution and the amino acid standard solution were analyzed (PDA detector, 260 nm) using the UPLC System (Waters Corporation). As a stationary phase, the Waters AccQ-Tag Ultra Column 100-2.1 mm (1.7 μm) was used, and as a mobile phase, the AccQ-Tag Ultra Eluent A and AccQ-Tag Ultra Eluent B were used at a composition ratio of 99.9% of A for 0 to 0.54 min; 82.5% of A for 7.74 to 8.5 min; 40.4% of A for 8.5 to 8.7 min; 99.9% of A for 8.7 to 10 min. As a result, the peaks of each amino acid were observed, and the contents of each amino acid were quantified using a calibration curve method for each peak. The total amount of all the detected amino acids was considered as the total amino acid content in the extracts. The measurement results are shown in Table 2 and FIG. 1.

TABLE 2

Total amino acid content (unit: %)

| Duration of light-shielding | No light-shielding (Comparative Example 2) | 70% light-shielding (Comparative Example 4) | 90% light-shielding (Example 4) | 95% light-shielding (Example 5) | 99% light-shielding (Example 2) |
|---|---|---|---|---|---|
| 1 day | 2.6 | 2.6 | 2.6 | 2.6 | 2.6 |
| 5 days | 2.8 | 2.8 | 3.0 | 3.1 | 3.3 |
| 10 days | 2.1 | 3.2 | 3.9 | 4.2 | 4.8 |
| 15 days | 0.7 | 2.7 | 4.3 | 4.6 | 5.2 |
| 20 days | 0.8 | 2.4 | 3.6 | 5.0 | 6.9 |
| 25 days | 0.5 | 1.6 | 3.0 | 5.7 | 7.1 |

As shown in Table 2, although the green tea cultivated by the general light-shielding cultivation method (Comparative Example 4) showed an increase in the amino acid content as compared with the green tea cultivated without light-shielding treatment (Comparative Example 2), it can be seen that the amino acid content tended to decrease as the light-shielding duration was prolonged.

In the case of the green tea cultivated without light-shielding treatment, as the tea leaves grew, the total amino acid content was 2.6% at the beginning of growth and slightly increased to 2.8% after 5 days, but thereafter, the total amino acid content tended to decrease continuously.

Figure 1:
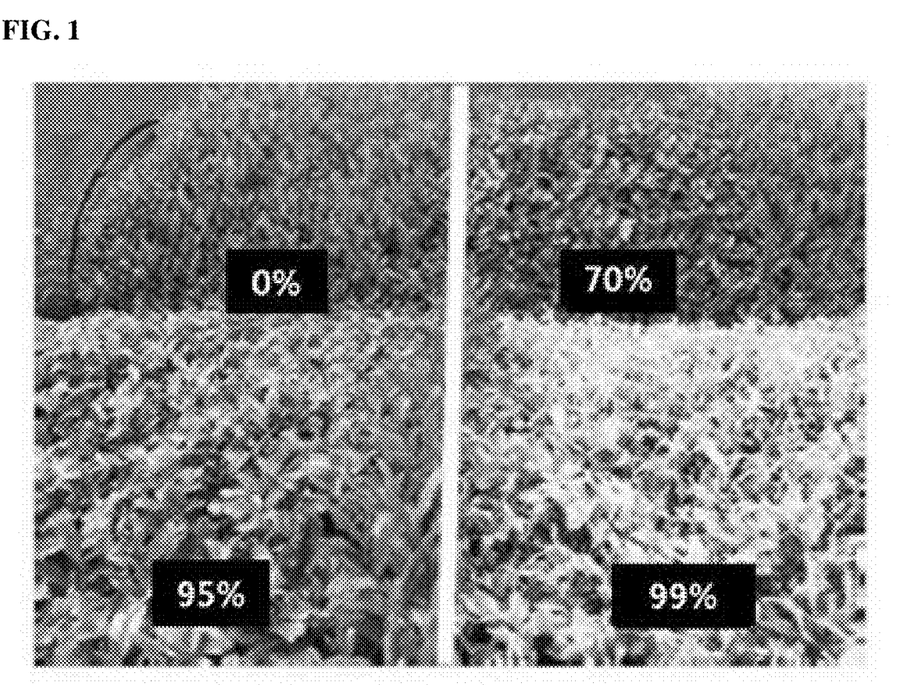
FIG. 1 shows the color of tea leaves according to the light-shielding rate during light-shielding cultivation.

In the case of the general light-shielding cultivation method (light-shielding rate of 70%), the total amino acid content was 3.2% when the light-shielding period was 10 days, indicating that the total amino acid content increased, but thereafter, the total amino acid content tended to decrease continuously. Also, as shown in FIG. 1, it can be seen that the green tea leaves had the darkest green color when the light-shielding rate was 70%.

In the case of the extreme light-shielding cultivation method under a light-shielding rate of 90%, the total amino acid content was the highest when the light-shielding duration was 15 days, and at this time, the total amino acid content was increased by more than 6 times as compared to the green tea cultivated without light-shielding treatment.

In particular, in the case of the extreme light-shielding cultivation method with a light-shielding rate of 95% or more, the total amino acid content continuously increased in all cultivation periods.

Specifically, the total amino acid content was only 0.5% in the case of no light-shielding cultivation method and 1.6% in the case of the general light-shielding cultivation method when the light-shielding duration was 25 days. However, in the case of the extreme light-shielding cultivation method with a light-shielding rate of 99%, it was confirmed that the amino acid content was 7.1%, which was increased by at least 4.5 times (compared to the general light-shielding method method) to 14.2 times (compared to no light-shielding treatment).

Thus, it was confirmed that the green tea cultivated by the extreme light-shielding cultivation method under a light-shielding rate of 90% or more had a significantly increased amino acid content as compared with the green tea cultivated without light-shielding treatment or by the general light-shielding cultivation method, and when the light-shielding rate was 95% or more, the amino acid content increased sharply as the light-shielding duration was prolonged.

2. Analysis of Catechin Content

The catechin content was determined by quantifying each of 8 kinds of catechin (gallocatechin, epigallocatechin, catechin, epicatechin, epigallocatechin gallate, gallocatechin gallate, epicatechin gallate and catechin gallate) via a simultaneous analysis, and the total amount was determined. The extracts were dissolved in 50% methanol to make a solution having a concentration of 1,000 ppm, and the components were analyzed (2996 PDA detector, manufactured by Waters Corporation) using HPLC (2695 model, manufactured by Waters Corporation). As a stationary phase, the Mightysil RP-18 GP 250-4.6 mm (5 μm) column manufactured by Kanto Chemical was used, and as a mobile phase, the composition ratios shown in Table 3 below were used. For the mixtures of 8 kinds of catechin, a derivatization reaction was performed in the same manner as the test solution by appropriately adjusting the concentration according to the content of each catechin in the extracts.

TABLE 3

| Time (min) | A: 0.1% acetic acid solution | B: Acetonitrile |
|---|---|---|
| 0 | 90 | 10 |
| 10 | 90 | 10 |
| 30 | 85 | 15 |
| 42 | 80 | 20 |
| 44 | 5 | 95 |
| 45 | 5 | 95 |
| 49 | 90 | 10 |
| 50 | 90 | 10 |

As a result, the peaks for each catechin were observed, and the content of each catechin was quantified using a calibration curve method for each peak. The total amount of all the detected catechin was considered as the total catechin content in the extract. The measurement results are shown in Table 4 below.

TABLE 4

| Duration of light-shielding | Total catechin content (Unit: %) | | | | |
|---|---|---|---|---|---|
| | No light-shielding | 70% light-shielding | 90% light-shielding | 95% light-shielding | 99% light-shielding |
| 1 day | 17 | 17 | 17 | 17 | 17 |
| 5 days | 16 | 16 | 14 | 15 | 15 |

TABLE 4-continued

Total catechin content (Unit: %)

| Duration of light-shielding | No light-shielding | 70% light-shielding | 90% light-shielding | 95% light-shielding | 99% light-shielding |
|---|---|---|---|---|---|
| 10 days | 15 | 15 | 14 | 14 | 15 |
| 15 days | 14 | 12 | 13 | 12 | 12 |
| 20 days | 14 | 12 | 12 | 12 | 11 |
| 25 days | 13 | 11 | 11 | 12 | 10 |

As shown in Table 4, it was confirmed that although the catechin contents of the green tea cultivated by the extreme light-shielding cultivation method tended to decrease slightly as the light-shielding rate was increased and the light-shielding duration was prolonged, the degree of decrease was not significant, and they were at almost the same level.

3. Comparison of Color of Tea Leaves According to Light-Shielding Rate

Figure 2:
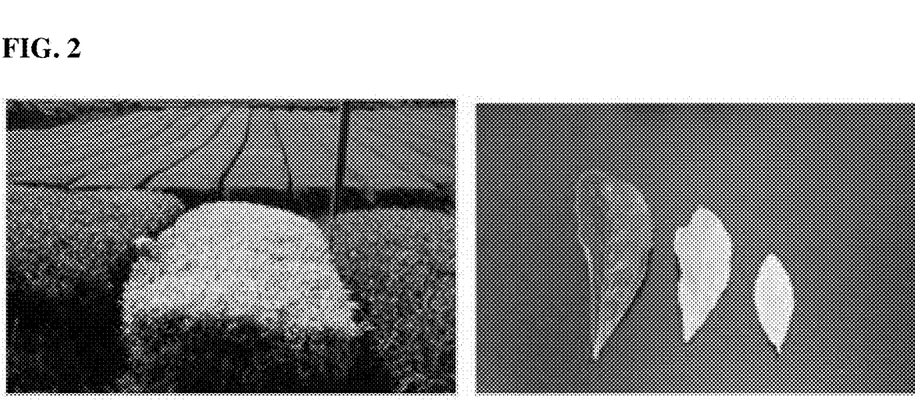
FIG. 2 shows the tea leaves cultivated by extreme light-shielding for 25 days with a light-shielding rate of 99%.
Figure 3:
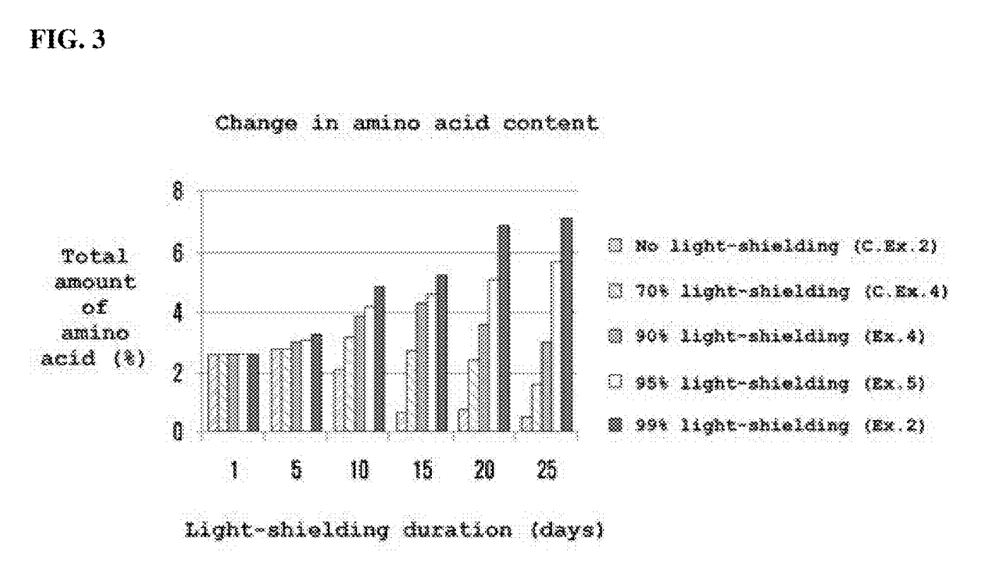
FIG. 3 is a graph showing the change in amino acid content in the green tea extract according to the light-shielding rate and light-shielding duration.
Figure 4:
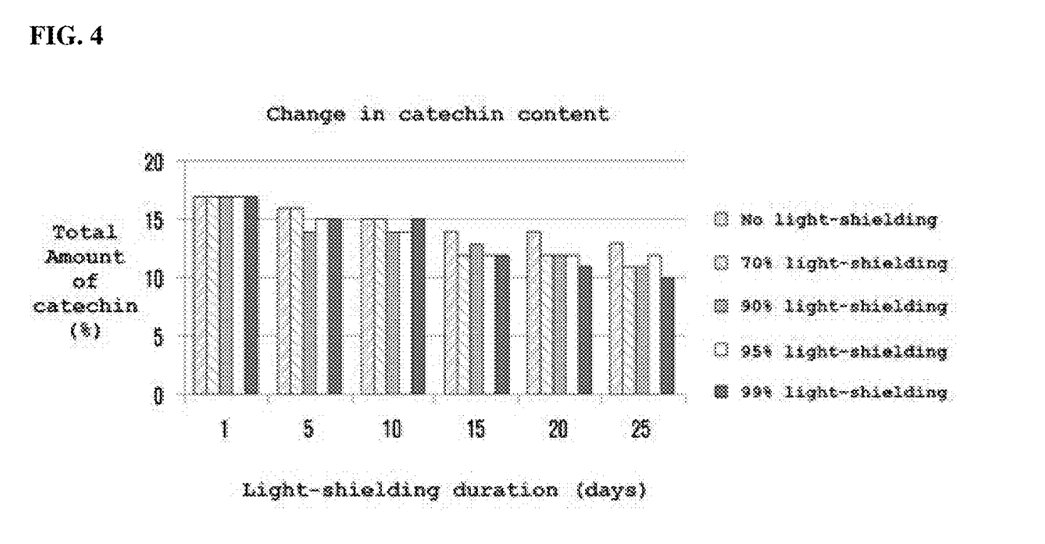
FIG. 4 is a graph showing the change in catechin content in the green tea extract according to the light-shielding rate and light-shielding duration.

Tea leaves of green tea cultivated by varying the light-shielding rates are shown in FIGS. 1 and 2.

As shown in FIG. 1, the green tea cultivated by the general light-shielding cultivation method with a light-shielding rate of 70% showed the darkest green color.

In addition, it can be confirmed that when the green teas were cultivated by extreme light-shielding with a light-shielding rate of 99%, the color of the tea leaves changed from green to clear white.

[Test Example 2] Determination of Optimal Light-Shielding Period

In the general light-shielding cultivation, the light-shielding treatment for Camellia sinensis L. is typically carried out at 1 stem-2 leaf stage to 3 leaf stage during the growing of the tea buds.

The following evaluation was carried out in order to determine the optimal light-shielding treatment period based on the results of the previous experiments that the contents of the amino acid and other oil-soluble ingredients are maximized, and that the color of the tea leaves changes to white depending on the light-shielding rate.

The 99% light-shielding treatment was carried out at each growing period of the tea buds (1 stem-1 leaf stage, 1 stem-2 leaf stage, 1 stem-3 leaf stage, 1 stem-4 leaf stage, and 1 stem-5 leaf stage), and the total amino acid content was analyzed according to the treatment duration. The results are shown in Table 5 below.

TABLE 5

Change in total amino acid content according to light-shielding treatment period of Camellia sinensis L. treated with light-shielding rate of 99%

| Light-shielding treatment period/ Treatment duration | Total amino acid content (%) | | | | |
|---|---|---|---|---|---|
| | 1 day | 7 days | 14 days | 21 days | 27 days |
| 1 stem-1 leaf base | 2.6 | 5.3 | 8.1 | 12.1 | 4.6 |
| 1 stem-2 leaf bases | 2.6 | 4.7 | 5.2 | 4.9 | 2.1 |
| 1 stem-3 leaf bases | 2.6 | 4.1 | 4.9 | 3.2 | 1.6 |
| 1 stem-4 leaf bases | 2.6 | 3.4 | 3.6 | 2.4 | 1.2 |
| 1 stem-5 leaf bases | 2.6 | 2.3 | 1.9 | 1.1 | 0.8 |

As shown in Table 5, the total amino acid content was 12.1% for the treatment period of 21 days in the period of 1 stem-1 leaf base, which was significantly higher than those observed under other light-shielding treatment periods. In addition, in all treatment durations, the amino acid content at the period of 1 stem-1 leaf base was the highest compared to those observed under other treatment periods.

In the period of 1 stem-1 leaf base, the total amino acid content was continuously increased until $21^{st}$ day of the treatment duration and rapidly decreased thereafter. This showed the tendency that the amino acid content increased for a certain duration of time and rapidly decreased, although there was a difference in each light-shielding treatment period.

Based on these results, it can be seen that the optimal conditions of the cultivation for producing new high-functional tea leaves and tea leaves with distinctive colors by extreme light-shielding are as follows: light-shielding rate of 99%, light-shielding treatment period of 1 stem-1 leaf base to 1 stem-3 leaf bases, and light-shielding treatment duration of about 21 days.

[Test Example 3] Analysis of Total Amino Acid Content in Extracts (Difference According to Light-Shielding Cultivation and Extraction Solvent)

The total amino acid content in the green tea extracts were analyzed in the same manner as in Test Example 1, except that Examples 1, 2 and 6 (each with light-shielding duration of 21 days) and Comparative Examples 1 (growth of 21 days) to 4 were used (light-shielding duration of 21 days). The analysis results are shown in Table 6 below.

TABLE 6

| Name of samples | Total amino acid (%) |
|---|---|
| Example 1 (extract of green tea cultivated by extreme light-shielding using 70% ethanol) | 11.2 |
| Example 2 (extract of green tea cultivated by extreme light-shielding through low-speed and low-temperature extraction using water) | 18.2 |
| Example 5 (extract of green tea cultivated by extreme light-shielding through low-temperature leaching using water) | 14.1 |

TABLE 6-continued

| Name of samples | Total amino acid (%) |
| --- | --- |
| Comparative Example 1 (extract of green tea cultivated without light-shielding treatment using 70% ethanol) | 3.7 |
| Comparative Example 2 (extract of green tea cultivated by without light-shielding treatment through low-speed and low-temperature extraction using water) | 5.8 |
| Comparative Example 3 (extract of green tea cultivated by general light-shielding using 70% ethanol) | 5.9 |
| Comparative Example 4 (extract of green tea cultivated by general light-shielding using water) | 8.7 |

As shown in Table 6, the total amino acid content in the extract of green tea cultivated by extreme light-shielding was remarkably increased compared to that of the extract of green tea cultivated by general light-shielding. In particular, it can be found that when the low-speed and low temperature extraction was carried out using water as the extraction solvent, the amount of extracted amino acid was further increased.

[Test Example 4] Confirmation of Expression of Moisturizing Genes

The effect of the extract of green tea cultivated by extreme light-shielding according to the present invention on the expression of two genes, i.e., loricrin and involucein, known to be related to skin moisturizing power was confirmed by the following method.

Keratinocytes were grown using the KGM-gold (Lonza, #00192151) medium, and subsequently, 25000 cells were seeded in a 6-well plate. On the next day, each extract of Examples 1 and 2 and Comparative Examples 1 and 3 was diluted 1000 times in a medium. The cells were treated with the extract and cultured for 1 day, and then the cells were collected. In order to extract RNA using TRIzol, the collected cells (about $1 \times 10^5$ cells) were added to a tube, 500 µl of TRIzol was added thereto, and the cells were homogenized at room temperature for 5 minutes. 100 µl of chloroform was added to each tube, mixed by shaking with a hand for 15 seconds, allowed to stand at room temperature for 3 minutes, and then centrifuged at 15,000×g for 15 minutes at 4° C. After only transferring the supernatant to a new tube, 250 µl of isopropyl alcohol was added thereto, mixed well, allowed to stand at room temperature for 10 minutes, and then centrifuged at 15,000×g for 10 minutes at 4° C. After discarding all supernatant, the remaining pellet was resuspended in 500 µl of 75% alcohol, subjected to vortexing, and then centrifuged at 7500×g for 5 minutes at 4° C. After carefully discarding the supernatant, the remaining pellet was well dried, and deionized water was added to the pellet to dissolve the RNA and quantified at 260 nm. In order to synthesize cDNA using the total RNA, 2 µl of oligo (dT) was added to 4 µg of the total RNA, allowed to react at 70° C. for 10 minutes and quickly cooled. DTT, dNTP, 10×RT buffer solution, $MgCl_2$, RNAase Out were added and allowed to react for 2 minutes at 42° C., and subsequently, Superscript III RT was added and allowed to react for 60 minutes at 50° C. 165 µl of deionized water was added to 35 µl of the synthesized cDNA mixture and diluted to a total volume of 200 µl. In order to proceed with qPCR, 5 µl of cDNA mixture+4 µl of deionized water+1 µl of each of Taqman primer (Control gene; RPLP0, Experimental genes; loricrin, involucrin)+10 µl of Taqman 2× Universal PCR Master Mix (#4304437, manufactured by ABI) were mixed, and the total of 20 µl was added to each PCR tube and the tubes were loaded into a real-time PCR instrument (model name: 7500fast, manufactured by ABI). The reaction setup was as follows: 1. Holding stage: 95° C. (10 min); 2. Cycling stage: 95° C. (15 sec)+60° C. (60 sec), repeated for 40 cycles. As the Taqman primer used at this time, a commercially available primer composed of fluorescent molecule FAM as a reporter and NFQ-MGB as a quencher was used.

The results are shown in Tables 7 and 8 below.

TABLE 7

| loricrin | Control Group | Comparative Example 1(ppm) | | | Comparative Example 3(ppm) | | | Example 1(ppm) | | | Example 2(ppm) | | |
| --- | --- | --- | --- | --- | --- | --- | --- | --- | --- | --- | --- | --- | --- |
| | | 6 | 12 | 25 | 6 | 12 | 25 | 6 | 12 | 25 | 6 | 12 | 25 |
| Average (AVR) | 1.00 | 1.04 | 1.92 | 3.00 | 1.14 | 2.45 | 3.56 | 1.27 | 2.74 | 4.45 | 1.44 | 2.98 | 4.96 |
| Standard deviation (STD) | 0.04 | 0.14 | 0.26 | 0.25 | 0.15 | 0.15 | 0.08 | 0.08 | 0.17 | 0.45 | 0.09 | 0.11 | 0.17 |

TABLE 8

| Involucrin | Control Group | Comparative Example 1 (ppm) | | | Comparative Example 3 (ppm) | | | Example 1 (ppm) | | | Example 2 (ppm) | | |
| --- | --- | --- | --- | --- | --- | --- | --- | --- | --- | --- | --- | --- | --- |
| | | 6 | 12 | 25 | 6 | 12 | 25 | 6 | 12 | 25 | 6 | 12 | 25 |
| Average (AVR) | 1.00 | 0.69 | 0.83 | 0.94 | 0.47 | 1.02 | 1.23 | 0.51 | 1.25 | 1.99 | 0.68 | 1.59 | 2.31 |
| Standard deviation (STD) | 0.04 | 0.05 | 0.00 | 0.02 | 0.01 | 0.03 | 0.09 | 0.03 | 0.07 | 0.02 | 0.00 | 0.04 | 0.05 |

As shown in Tables 7 and 8, it can be confirmed that the expression level of both genes was increased in all cases upon treatment with the green tea extract. In particular, the extract of green tea cultivated by extreme light-shielding showed remarkably excellent efficiency compared to the extract of general green tea.

[Test Example 5] Collagenase (MMP-1) Inhibitory Effect

The collagenase production inhibitory effect of the present invention on wrinkle improvement was measured in comparison with retinoic acid.

Human fibroblasts were seeded at 5,000 cells/well in a 96-well microtiter plate filled with a Dulbecco's modified eagle's medium (DMEM) containing 2.5% fetal bovine serum and cultured in a 5% $CO_2$ incubator at 37° C. until they grew by about 70 to 80%. The cells were treated with the extracts of Examples 1 and 2 and Comparative Examples 1 and 3 or retinoic acid at a concentration of 10 μg/ml for 24 hours, and the cell culture was collected.

The production yield of collagenase in the collected cell culture was measured using a collagenase measurement instrument commercially available (Catalog #. RPN 2610, manufactured by Amersham Pharma Inc., USA). Firstly, the collected cell culture added to a 96-well plate uniformly coated with the primary collagenase antibodies and then subjected to an antigen-antibody reaction in a thermostat container for 3 hours. After 3 hours, the secondary collagenase antibodies coupled to the chromophores are added to the 96-well plate and then allowed to react for more 15 minutes. After 15 minutes, a color-causing substance (3,3', 5,5'-tetramethylbenzidine, Sigma) was added to the 96-well plate to cause coloration at the room temperature for 15 minutes, and then 1M sulfuric acid was added to terminate the coloration reaction so that the reaction mixture became yellow. The intensity of yellowness in the reaction mixture was varied depending on the progress of the reaction.

The absorbance of the yellow-colored 96-well plate was measured at 405 nm with a spectrophotometer, and the expression level of collagenase was calculated according to the following Mathematical Formula 1. The results are shown in Table 9. At this time, the absorbance of the cell culture collected from the group not treated with the composition was considered as the control group.

Expression level of collagenase (%)=Absorbance of substance-treated cell group/Absorbance of control group×100   [Mathematical Formula 1]

TABLE 9

| Compounds | Expression level (%) |
|---|---|
| Non-treated group | 100 |
| Retinoic acid | 75 |
| Comparative Example 1 | 73 |
| Comparative Example 3 | 77 |
| Example 1 | 73 |
| Example 2 | 76 |

From the results shown in Table 9, it can be seen that the collagenase expression level of the extract of green tea cultivated by extreme light-shielding was similar to that of retinoic acid. Accordingly, the collagenase expression inhibition effect of the extract of green tea cultivated by extreme light-shielding was also similar to that of retinoic acid, which is known as a collagenase expression inhibitor.

From these results, it can be confirmed that the extract of green tea cultivated by extreme light-shielding of the present invention has an effect of inhibiting matrix metalloprotease (MMP-1).

[Test Example 6] Measurement of Inhibitory Effect of Elastase Activity

The inhibitory effect of elastase activity of the extract of green tea cultivated by extreme light-shielding on anti-aging was measured in comparison with that of EGCG. The elastase and the substrate used herein were purchased from Sigma-Aldrich, U.S.A. (Cat. No. E0127).

The inhibitory function of elastase activity was tested according to the following method.

In a 96-well plate, ginsenoside Rh4 (200 μL) and 50 μL of a 20 μg/mL elastase type III solution were mixed with a 10 mg/L Tris-HCL buffer solution (pH 8.0). EGCG 250 μM was used as a positive control, and purified water was used as a non-treated group, which was a negative control. Then, 100 μL of 0.4514 mg/mL N-SUCCINYL-ALA-ALA-ALA-p-NITROANILIDE prepared with the buffer solution was added to the mixture and allowed to react at 25° C. for 15 minutes. After completion of the reaction, the absorbance at the wavelength of 415 nm was measured. A blank test was conducted in the same manner for correction.

The inhibitory function of elastase was calculated according to the following Mathematical Formula 2, and the results are shown in Table 10.

Inhibition Ratio of Elastase Activity[%]={1−(C−D)/ A−B}}×100   [Mathematical Formula 2]

A: Absorbance at the wavelength of 415 nm in the absence of the test material and in the presence of enzyme B: Absorbance at the wavelength of 415 nm in the absence of the test material and enzyme C: Absorbance at the wavelength of 415 nm in the presence of the test material and enzyme D: Absorbance at the wavelength of 415 nm in the presence of the test material and in the absence of enzyme

TABLE 10

| Compound | Inhibition level (%) |
|---|---|
| Non-treated group | 0 |
| EGCG | 65 |
| Comparative Example 1 | 70 |
| Comparative Example 3 | 66 |
| Example 1 | 67 |
| Example 2 | 69 |

As can be seen from Table 10, it can be confirmed that the inhibition level of elastase activity of the extract of green tea cultivated by extreme light-shielding was similar to that of EGCG which is known as an elastase inhibitor. Accordingly, the extract of green tea cultivated by extreme light-shielding of the present invention has an excellent inhibitory effect of elastase activity.

[Test Example 7] Confirmation of Expression of Barrier-Function Enhancing Gene

The effect of the extract of green tea cultivated by extreme light-shielding according to the present invention on the expression of caspase-14 gene, known to be involved in enhancing skin barrier function was confirmed by the following method.

Keratinocytes were grown using the KGM-gold (Lonza, #00192151) medium, and subsequently, 25000 cells were seeded in a 6-well plate. On the next day, each extract of Examples 1 and 2 and Comparative Examples 1 and 3 was diluted 1000 times in a medium. The cells were treated with the extract and cultured for 1 day, and then the cells were collected. In order to extract RNA using TRIzol, the collected cells (about $1\times10^5$ cells) were added to a tube, 500 μl of TRIzol was added thereto, and the cells were homogenized at room temperature for 5 minutes. 100 μl of chloroform was added to each tube, mixed by shaking with a hand for 15 seconds, allowed to stand at room temperature for 3 minutes, and then centrifuged at 15,000×g for 15 minutes at 4° C. After only transferring the supernatant to a new tube, 250 μl of isopropyl alcohol was added thereto, mixed well, allowed to stand at room temperature for 10 minutes, and then centrifuged at 15,000×g for 10 minutes at 4° C. After discarding all supernatant, the remaining pellet was resuspended in 500 μl of 75% alcohol, subjected to vortexing, and then centrifuged at 7500×g for 5 minutes at 4° C. After carefully discarding the supernatant, the remaining pellet was well dried, and deionized water was added to the pellet to dissolve the RNA and quantified at 260 nm. In order to synthesize cDNA using the total RNA, 2 μl of oligo (dT) was added to 4 μg of the total RNA, allowed to react at 70° C. for 10 minutes and quickly cooled. DTT, dNTP, 10× RT buffer solution, $MgCl_2$, RNAase Out were added and allowed to react for 2 minutes at 42° C., and subsequently, Superscript III RT was added and allowed to react for 60 minutes at 50° C. 165 μl of deionized water was added to 35 μl of the synthesized cDNA mixture and diluted to a total volume of 200 μl. In order to proceed with qPCR, 5 μl of cDNA mixture+4 μl of deionized water+1 μl of each of Taqman primer (Control gene; RPLP0, Experimental gene; caspase-14)+10 μl of Taqman 2× Universal PCR Master Mix (#4304437, manufactured by ABI) were mixed, and the total of 20 μl was added to each PCR tube and the tubes were loaded into a real-time PCR instrument (model name: 7500fast, manufactured by ABI). The reaction setup was as follows: 1. Holding stage: 95° C. (10 min); 2. Cycling stage: 95° C. (15 sec)+60° C. (60 sec), repeated for 40 cycles. As the Taqman primer used at this time, a commercially available primer composed of fluorescent molecule FAM as a reporter and NFQ-MGB as a quencher was used.

The results are shown in Table 11 below.

[Test Example 8] Confirmation of Expression of Skin Damage Suppressing or Skin Protecting Gene The effect of the extract of green tea cultivated by extreme light-shielding according to the present invention on the expression of histidase gene, known to be involved in skin damage suppression or skin protection was confirmed by the following method.

Keratinocytes were grown using the KGM-gold (Lonza, #00192151) medium, and subsequently, 25000 cells were seeded in a 6-well plate. On the next day, each extract of Examples 1 and 2 and Comparative Examples 1 and 3 was diluted 1000 times in a medium. The cells were treated with the extract and cultured for 1 day, and then the cells were collected. In order to extract RNA using TRIzol, the collected cells (about $1\times10^5$ cells) were added to a tube, 500 μl of TRIzol was added thereto, and the cells were homogenized at room temperature for 5 minutes. 100 μl of chloroform was added to each tube, mixed by shaking with a hand for 15 seconds, allowed to stand at room temperature for 3 minutes, and then centrifuged at 15,000×g for 15 minutes at 4° C. After only transferring the supernatant to a new tube, 250 μl of isopropyl alcohol was added thereto, mixed well, allowed to stand at room temperature for 10 minutes, and then centrifuged at 15,000×g for 10 minutes at 4° C. After discarding all supernatant, the remaining pellet was resuspended in 500 μl of 75% alcohol, subjected to vortexing, and then centrifuged at 7500×g for 5 minutes at 4° C. After carefully discarding the supernatant, the remaining pellet was well dried, and deionized water was added to the pellet to dissolve the RNA and quantified at 260 nm. In order to synthesize cDNA using the total RNA, 2 μl of oligo (dT) was added to 4 μg of the total RNA, allowed to react at 70° C. for 10 minutes and quickly cooled. DTT, dNTP, 10×RT buffer solution, $MgCl_2$, RNAase Out were added and allowed to react for 2 minutes at 42° C., and subsequently, Superscript III RT was added and allowed to react for 60 minutes at 50° C. 165 μl of deionized water was added to 35 μl of the synthesized cDNA mixture and diluted to a total volume of 200 μl. In order to proceed with qPCR, 5 μl of cDNA mixture+4 μl of deionized water+1 μl of each of Taqman primer (Control gene; RPLP0, Experimental gene; histidase)+10 μl of Taqman 2× Universal PCR Master Mix (#4304437, manufactured by ABI) were mixed, and the total of 20 μl was added to each PCR tube and the tubes were loaded into a real-time PCR instrument (model name: 7500fast, manufactured by ABI). The reaction setup was as

TABLE 11

| Caspase | Control | Comparative Example 1(ppm) | | | Comparative Example 3(ppm) | | | Example 1(ppm) | | | Example 2(ppm) | | |
|---|---|---|---|---|---|---|---|---|---|---|---|---|---|
| 14 | group | 6 | 12 | 25 | 6 | 12 | 25 | 6 | 12 | 25 | 6 | 12 | 25 |
| Average (AVR) | 1.00 | 1.80 | 2.26 | 2.86 | 2.02 | 2.54 | 2.98 | 2.20 | 2.95 | 3.36 | 2.31 | 3.07 | 3.74 |
| Standard Deviation (STD) | 0.04 | 0.05 | 0.19 | 0.17 | 0.23 | 0.28 | 0.10 | 0.11 | 0.05 | 0.04 | 0.08 | 0.19 | 0.11 |

As shown in Table 11, the expression level of the caspase-14 gene was increased in all cases upon treatment with the green tea extract. In particular, the extract of green tea cultivated by extreme light-shielding showed excellent efficiency compared to the extract of general green tea.

follows: 1. Holding stage: 95° C. (10 min); 2. Cycling stage: 95° C. (15 sec)+60° C. (60 sec), repeated for 40 cycles. As the Taqman primer used at this time, a commercially available primer composed of fluorescent molecule FAM as a reporter and NFQ-MGB as a quencher was used.

The results are shown in Table 12 below.

TABLE 12

| Histidase | Control Group | Comparative Example 1(ppm) | | | Comparative Example 3(ppm) | | | Example 1(ppm) | | | Example 2(ppm) | | |
|---|---|---|---|---|---|---|---|---|---|---|---|---|---|
| | | 6 | 12 | 25 | 6 | 12 | 25 | 6 | 12 | 25 | 6 | 12 | 25 |
| Average (AVR) | 1.00 | 0.79 | 0.95 | 1.12 | 0.80 | 1.03 | 1.26 | 0.88 | 1.13 | 1.57 | 0.91 | 1.23 | 1.75 |
| Standard Deviation (STD) | 0.04 | 0.09 | 0.08 | 0.08 | 0.02 | 0.12 | 0.03 | 0.11 | 0.14 | 0.03 | 0.05 | 0.06 | 0.10 |

As shown in Table 12, it can be seen that the expression level of histidase gene was increased in all cases upon treatment with the green tea extract. In particular, the extract of green tea cultivated by extreme light-shielding showed excellent efficiency compared to the extract of general green tea.

The invention claimed is:

1. A method for improving a skin condition comprising applying externally a skin external composition to a skin of subject,
   wherein the skin external composition comprises an extract of green tea leaves as an active ingredient,
   wherein the green tea leaves are obtained from a tea plant (*Camellia sinensis* L.) cultivated by an extreme light-shielding cultivation method under a light-shielding rate of 90% or more,
   wherein the extract of green tea leaves is obtained by an extraction using water as an extraction solvent at a temperature of 4° C. or less and at a rate of about 100 mL per hour per 100 g of powder of the green tea leaves for 10 hours, and
   wherein the improving a skin condition is one or more of the following (a)-(f):
   (a) skin moisturization;
   (b) skin anti-aging;
   (c) improving skin wrinkles;
   (d) improving skin elasticity;
   (e) improving skin barrier function; and
   (f) suppressing skin damage or protecting the skin.

2. The method according to claim 1, wherein a content of the active ingredient is 0.0001 to 40% by weight based on the total weight of the skin external composition.

3. The method according to claim 1, wherein the skin external composition has a formulation selected from the group consisting of a softening cosmetic water, astringent cosmetic water, nourishing cosmetic water, nourishing cream, massage cream, essence, eye cream, eye essence, cleansing cream, cleansing foam, cleansing water, facial pack, powder, body lotion, body cream, body oil, and body essence.

4. The method according to claim 1, wherein the light-shielding cultivation method employs the light-shielding rate of 95% or more.

5. The method according to claim 1, wherein the light-shielding cultivation method employs the light-shielding rate of 98% or more.

6. The method according to claim 1, wherein the light-shielding cultivation method employs the light-shielding rate of 99% or more.

7. The method according to claim 1, wherein the light-shielding cultivation is carried out for a duration of 10 days to 25 days.

8. The method according to claim 1, wherein the light-shielding cultivation is carried out for a duration of 15 days to 21 days.

9. The method according to claim 4, wherein the light-shielding cultivation is carried out for a duration of 10 days to 25 days.

10. The method according to claim 4, wherein the light-shielding cultivation is carried out for a duration of 15 days to 21 days.

* * * * *